United States Patent [19]

Smit et al.

[11] Patent Number: 5,248,800

[45] Date of Patent: Sep. 28, 1993

[54] PROCESS FOR THE PREPARATION OF TRIALKYL GALLIUM COMPOUNDS

[75] Inventors: Cornelis J. Smit; Erris W. J. Van Hunnik; Gerbrand J. M. Van Eijden, all of Arnhem, Netherlands

[73] Assignee: Shell Research Limited, London, United Kingdom

[21] Appl. No.: 971,874

[22] Filed: Nov. 5, 1992

[30] Foreign Application Priority Data

Nov. 19, 1991 [EP] European Pat. Off. .......... 91203017

[51] Int. Cl.$^5$ .............................................. C07F 5/00
[52] U.S. Cl. ...................................................... 556/1
[58] Field of Search ............................................ 556/1

[56] References Cited

FOREIGN PATENT DOCUMENTS 0231568  1/1986  German Democratic Rep. .
1-301684 12/1989  Japan .
0388563  4/1976  U.S.S.R. .
2123423  2/1984  United Kingdom .

OTHER PUBLICATIONS

Jones et al., J. Chem. Soc. Dalton Trans., pp. 1047–1049 (1983).

Primary Examiner—Paul F. Shaver
Assistant Examiner—Porfirio Nazario

[57] ABSTRACT

A process for the preparation of trialkyl gallium compounds, in which an alloy of gallium and magnesium is contacted with an alkyl halide, the alloy having an atomic ratio of gallium to magnesium from about 1:1.6 to about 1:2.4.

10 Claims, No Drawings

PROCESS FOR THE PREPARATION OF TRIALKYL GALLIUM COMPOUNDS

FIELD OF THE INVENTION

The present invention relates to the preparation of trialkyl gallium compounds.

BACKGROUND OF THE INVENTION

Organogallium compounds, particularly trialkyl gallium compounds, have found increasing use in the semiconductor industry. In this industry a gallium compound is deposited onto a suitable substrate, generally together with one or more compounds of a Group 5 element, such as arsenic or phosphorus. The deposition of such compounds is carried out via the decomposition of organometallic compounds from the vapor phase. Such decomposition is known as Metal Organic Chemical Vapor Deposition (MOCVD). When epitaxial layers are grown from such decomposition the technique is better known as Metal Organic Vapor Phase Epitaxy (MOVPE).

A convenient route for the preparation of trialkyl gallium compounds is via the reaction of gallium (III) chloride with either a Grignard reagent, i.e., an alkyl magnesium halide, or an alkyl lithium compound. A disadvantage of these methods resides in the use of gallium (III) chloride which is difficult to obtain in the purity that is required for products used in the semiconductor industry. High purity gallium is available commercially and is therefore a suitable starting material for the preparation of trialkyl gallium compounds.

It is known to prepare trialkyl gallium compounds from alloys or mixtures of gallium and magnesium by reaction with alkyl halides according to the following reaction:

$$2Ga + 3Mg + 6RX \rightarrow 2R_3Ga + 3MgX_x,$$

in which R represents an alkyl group and X is halide. Such reactions not only require an excess of magnesium, but also a super-stoichiometric amount of alkyl halide. All this adds to the cost of the trialkyl gallium production. When a sub-stoichiometric amount of magnesium is used one would expect that the yield of trialkyl gallium compounds, based on original gallium, would decrease. Unreacted gallium would be present in the reaction product which would represent a considerable disadvantage because high purity gallium is expensive.

In U.K. patent specification No. 2,123,423 a process for the preparation of trimethylgallium or triethylgallium is described in which an alloy $Ga_2Mg_5$ is reacted with methyl iodide in the presence of an ether. The ether is a relatively volatile ether, such as diethyl ether, or an ether with a relatively high boiling point, e.g., di-isopentyl ether or diphenyl ether.

In Soviet Union author's certificate No. 325,847, trialkyl gallium compounds are prepared from stoichiometric mixtures or alloys of gallium and magnesium by reaction with an alkyl halide. The yields of trialkyl gallium compounds were up to 65%. It has now been found that the yield of trialkyl gallium is substantially increased if the Ga—Mg alloy used contains a particular excess of magnesium.

SUMMARY OF THE INVENTION

The present invention provides an improved process for the preparation of trialkyl gallium compounds, in which an alloy of gallium and magnesium is contacted with an alkyl halide, in which alloy the atomic ratio of gallium to magnesium is from about 1:1.6 to about 1:2.4.

The advantage of the invention over the process of the above Soviet reference is an increased yield of trialkyl gallium compounds. The advantages over the process of the above U.K. specification are an increased yield, a reduction of by-products such as magnesium and Grignard reagent, and a reduced requirement for alkyl halide.

DESCRIPTION OF THE INVENTION

The alloy employed in the process of the invention generally contains at least one intermetallic compound of gallium and magnesium. Such intermetallic compounds are $Ga_2Mg_5$, $GaMg_2$ and $GaMg$. The alloy suitably contains a mixture of such intermetallic compounds. Preferably, the alloy contains one or more of intermetallic compounds such that the atomic ratio of gallium to magnesium is from about 1:1.9 to about 1:2.3. Preferably, the alloy contains from about 40% wt to 100% wt of $GaMg_2$, provided the overall atomic ratio is within the above range. If the alloy is substantially $GaMg_2$ the yield of trialkyl gallium is excellent and the amount of by-products is small.

The halogen moiety of the alkyl halide is selected from chlorine, bromine or iodine. Especially alkyl bromides and alkyl iodides are advantageously used in the present process.

The alkyl groups in the trialkyl gallium compounds are straight-chain or are branched. Although the present process can be carried out with a wide variety of alkyl halides, including those having long chain alkyl groups, the preparation of trialkyl gallium compounds containing alkyl groups with up to 6 carbon atoms inclusive is preferred. The alkyl group of the alkyl halide has preferably from 1 to 5 carbon atoms. More preferably, the alkyl moiety is methyl or ethyl.

The reaction is carried out under mild conditions. The pressure may be atmospheric, but also subatmospheric or superatmospheric pressures are suitable. Generally, the pressure is from about 0.1 bar to about 10 bar. Largely for convenience, the process if preferably carried out at atmospheric pressure. The trialkyl compound is prepared under an inert atmosphere, e.g., under nitrogen, argon or helium. The reaction temperature will vary but will be below the decomposition temperature of the desired compound. The temperature is suitably from ambient to about 200° C. Preferably, the process is carried out at a temperature from about 50° C. to about 160° C.

The process is carried out in the presence of a solvent. Not only will the solvent ensure a homogeneous distribution of the reactants, but it also provides a convenient means for controlling the transfer of the heat evolved in the exothermic reaction. A variety of solvents is useful in the present process. Such solvents include aliphatic or aromatic hydrocarbons, such as pentane, hexane, heptane, benzene, toluene or xylene, amides, such as N,N-dimethylacetamide and dimethyl formamide. The ethers, which are cyclic or non-cyclic, are a preferred class of solvents and contain from 3 to 18 carbon atoms inclusive. Suitable ethers include dioxane or tetrahydrofuran and diethyl ether, diphenyl ether, di-isopropyl ether, di-isopentyl ether and mixtures thereof.

The alkyl halide is preferably used in a molar amount sufficient to convert all gallium. The amount of alkyl halide suitably ranges from about 3 moles to about 5 moles, preferably from about 4 moles to 4.5 moles per gram atom of gallium. Preferably, the molar amount of alkyl halide is twice the amount of magnesium in gram atoms.

After completion of the reaction the reaction mixture will contain the trialkyl gallium compound, magnesium halide and some Grignard reagent. The trialkyl compound is separated from the magnesium halide by conventional techniques including filtration and decantation. Conveniently, the trialkyl compound is recovered by distillation. After a first distillation a second fractional distillation may be applied. In the isolation of the trialkyl gallium compound from the reaction mixture by distillation, it may be advantageous to recover the first 1 percent to 10 percent by volume of the product separately. In such case the main fraction which is subsequently recovered as the desired product has an enhanced purity. The first fraction of the distilled product is recycled to the original reaction mixture, or is discarded. In order to avoid any possible thermal decomposition of the trialkyl compound, the distillation is carried out under atmospheric or subatmospheric pressure to lower the boiling point of the trialkyl compounds. The distillation pressure used depends to a large extent on the number of carbon atoms in the alkyl groups because such numbers influence the decomposition temperature and boiling point of the trialkyl compound. For distillation of trimethylgallium the pressure can be atmospheric. For trialkyl compounds with higher alkyl groups the decomposition temperature is often higher than the distillation temperature and thus the distillation pressure is preferably lower than 1 bar. The distillation pressures are suitably selected up to 1000 mbar, and is preferably from <1 mbar to about 500 mbar. In an alternate modification, the trialkylgallium compound is purified by the process disclosed in co-pending U.S. application Ser. No. 07/971,875, filed Nov. 5, 1992.

The invention is further illustrated by means of the following examples which should not be construed as limiting.

EXAMPLE 1

In each of a number of experiments, about 75 g of a magnesium-gallium alloy was added to 200 ml of di-isopentyl ether in an inert atmosphere. Methyl iodide was added to the mixture at a rate to maintain the temperature at about 140° C. After addition of the methyl iodide the reaction mixture was maintained at 70° C. overnight to allow the reaction to go to completion. The resulting suspension, containing $MgI_2$ and an adduct of the ether and trimethylgallium, was heated to about 110° C., at which temperature the adduct dissociated and distillation of trimethylgallium started. The distillation was stopped when the bottom temperature of the distillation mixture reached 195° C. Water was added to the remaining suspension and insoluble gallium was isolated and weighed. The yield of trimethylgallium was calculated as the difference of the amount of gallium in the suspension. The purity of the trimethylgallium was determined with $H^1$-NMR. The results of the experiments and some reaction conditions are indicated in the Table.

TABLE

| Experiment No. | Ga/Mg Molar Ratio in Alloy | Molar % Intermetallic Compound in Alloy | | | Molar Ratio | | Yield % |
|---|---|---|---|---|---|---|---|
| | | $Ga_2Mg_5$ | $GaMg_2$ | $GaMg$ | MeI:Ga | MeI:Mg | |
| 1 | 2.5 | 100 | — | — | 5 | 2 | 82 |
| 2 | 2.25 | 50 | 50 | — | 4.5 | 2 | 85 |
| 3 | 2.0 | — | 100 | — | 4 | 2 | 84 |
| 4 | 1.5 | — | 50 | 50 | 3 | 2 | 69 |
| 5 | 1.0 | — | — | 100 | 2 | 2 | 54 |

From the Table it is apparent that the atomic ratio of Ga to Mg has a significant effect on the yield of converted gallium. It is further shown that the amount of methyl iodide required in the reaction is reduced if the process is carried out in accordance with the invention. From experiment No. 4 it is apparent that the mere presence of $GaMg_2$ is not sufficient to obtain advantageous results.

COMPARATIVE EXPERIMENT

By a process substantially similar to that of Example 1, a physical mixture of pure magnesium and pure gallium (in an atomic ration of 2:1) was reacted with 4 molar equivalent of methyl iodide. A yield of only 15% of converted gallium was found.

EXAMPLE 2

A $GaMg_2$ alloy comprising about 100% of the intermetallic compound $GaMg_2$, was contacted with 3.5 equivalents of ethyl bromide in a mixture of diethyl ether and diphenyl ether as solvent. The reaction was exothermic and the rate of ethyl bromide addition was such that the temperature did not exceed 140° C. After all the ethyl bromide was added the reaction mixture was stirred for 16 hours at 100° C. to complete the formation of an adduct of triethylgallium and diethyl ether. Subsequently, the triethylgallium.diethyl ether adduct was distilled at a bottom temperature of 100°-140° C. Throughout the distillation the pressure was decreased to maintain the desired distillation rate, starting from 100 mbar and decreasing to 25 mbar. The yield of TEG.diethyl ether was 95% based on the gallium originally present in the alloy.

EXAMPLE 3

$GaMg_{1.9}$ alloy, comprising about 90% of the intermetallic compound $GaMg_2$, was contacted with 3.8 equivalents of methyl iodide in di-isopentyl ether as solvent. The reaction was exothermic and the rate of the methyl iodide addition was such that the temperature of mixture increased to 140° C. After all the methyl iodide was added, the reaction mixture was stirred for 16 hours at 75° C. Trimethyl gallium was distilled from the reaction mixture at atmospheric pressure at a bottom temperature of 110°-195° C. The yield of the desired product was 77%, based on gallium originally present in the alloy.

What is claimed is:

1. A process for the preparation of trialkyl gallium wherein an alloy of gallium and magnesium is contacted with alkyl halide in the presence of solvent, the alloy having an atomic ratio of gallium to magnesium from about 1:1.6 to about 1:2.4.

2. The process of claim 1 wherein alkyl halide is alkyl bromide or alkyl iodide.

3. The process of claim 2 wherein alkyl is alkyl of up to 6 carbon atoms inclusive.

4. The process of claim 3 wherein the solvent is an ether.

5. The process of claim 4 wherein the atomic ratio of gallium to magnesium is from about 1:1.9 to about 1:2.3.

6. The process of claim 4 wherein alkyl is methyl or ethyl.

7. The process of claim 6 wherein the alloy substantially is the intermetallic compound $GaMg_2$.

8. The process of claim 6 wherein the alkyl halide is alkyl iodide.

9. The process of claim 6 wherein the alkyl halide is methyl iodide.

10. The process of claim 6 wherein the alkyl halide is ethyl iodide.

* * * * *